United States Patent [19]

Heeres

[11] 4,101,666
[45] Jul. 18, 1978

[54] 1-(2-AR-4-R-1,3-DIOXOLAN-2-YLMETHYL-)IMIDAZOLES

[75] Inventor: Jan Heeres, Vosselaar, Belgium

[73] Assignee: Janssen Pharmaceutica N.V., Beerse, Belgium

[21] Appl. No.: 732,826

[22] Filed: Oct. 15, 1976

Related U.S. Application Data

[63] Continuation-in-part of Ser. No. 619,863, Oct. 6, 1975, abandoned, which is a continuation-in-part of Ser. No. 544,157, Jan. 27, 1975, Pat. No. 3,936,470.

[51] Int. Cl.$^2$ .................. C07D 405/06; A61K 31/33
[52] U.S. Cl. .................. 424/273 R; 260/340.9 R; 260/348.11; 260/348.49; 260/348.57; 260/348.63; 548/336
[58] Field of Search .................. 260/309; 424/273; 548/336

[56] References Cited

U.S. PATENT DOCUMENTS

| 3,575,999 | 4/1971 | Godefroi et al. | 260/309 |
| 3,717,655 | 2/1973 | Godefroi et al. | 260/309 |
| 3,936,470 | 2/1976 | Heeres | 260/309 |

Primary Examiner—Natalie Trousof
Attorney, Agent, or Firm—Salvatore R. Conte

[57] ABSTRACT 1-(2-Ar-4-R-1,3-dioxolan-2-ylmethyl)imidazoles, useful as antifungal and antibacterial agents.

12 Claims, No Drawings

1-(2-AR-4-R-1,3-DIOXOLAN-2-YLMETHYL-)IMIDAZOLES

CROSS-REFERENCE TO RELATED APPLICATIONS:

This is a continuation-in-part of my copending application, Ser. No. 619,863, filed Oct. 6, 1975, now abandoned, which in turn is a continuation-in-part of my application Ser. Nio. 544,157, filed Jan. 27, 1975, now issued as U.S. Pat. No. 3,936,470.

PRIOR ART

In U.S. Pat. Nos. 3,575,999 and 3,717,655 are described some 1-(2-aryl-1,3-dioxolan-2-ylmethyl-)imidazoles. The compounds of the present invention differ from the foregoing essentially by the nature of the R-substituent, present in the 4-position of the dioxolane group.

DESCRIPTION OF THE INVENTION

The invention relates to novel imidazole derivatives having the formula:

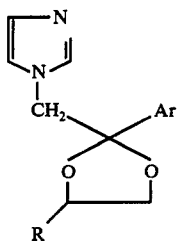

(I)

and the therapeutically acceptable acid addition salts thereof, wherein:

Ar is a member selected from the group consisting of phenyl, substituted phenyl, thienyl, halothienyl and naphthalenyl, and wherein said substituted phenyl is phenyl having from 1 to 3 substituents independently selected from the group consisting of halo, lower alkyl, lower alkyloxy, nitro and cyano; and R is a member selected from the group consisting of alkyloxymethyl wherein the alkylgroup has from 1 to 10 carbon atoms, alkenyl, alkenyloxymethyl, wherein said alkenyl has from 2 to 10 carbon atoms, hydroxymethyl, 2-propynyloxymethyl, halomethyl, arylmethyl and arylmethoxymethyl, wherein said aryl is a member selected from the group consisting of phenyl, substituted phenyl, naphthalenyl and mono- and di-halonaphthalenyl and wherein said substituted phenyl is phenyl having from 1 to 3 substituents independently selected from the group consisting of halo, loweralkyl, lower alkyloxy, cyano, nitro, phenyl, phenylmethyl, benzoyl, halobenzoyl, lower alkylcarbonyl, lower alkyloxycarbonyl and trifluoromethyl, provided that when more than 1 substituents are present only 1 thereof may be selected from the group consisting of phenyl, phenylmethyl, benzoyl and halobenzoyl.

More particularly, "alkyl" as used in the definition of alkyloxymethyl is meant to include straight and branch chained hydrocarbon radicals having from 1 to about 10 carbon atoms such as, for example, methyl, ethyl, propyl, 1-methylethyl, 1,1-dimethylethyl, butyl, pentyl, hexyl, heptyl, octyl, decyl and the like alkyls; "lower alkyl" as used herein has the meaning of a straight or branch chained alkyl radical having from 1 to about 6 carbon atoms, such as, for example, methyl, ethyl, propyl, 1-methylethyl, 1,1-dimethylethyl, butyl, pentyl, hexyl and the like alkyls; "alkenyl" as used herein refers to straight and branch chained alkenyl radicals having from 2 to about 10 carbon atoms, such as, for example, ethenyl, 2-propenyl, 2-butenyl, 3-butenyl, 2-pentenyl, 2-hexenyl, 2-decenyl and the like alkenyls; and the term "halo" is generic to halogens of atomic weight less than 127, i.e., fluoro, chloro, bromo and iodo.

The compounds of formula (I) are conveniently prepared by reacting imidazole (II) with an appropriate reactive ester of formula (III) wherein Ar and R are as previously defined and wherein W is a reactive ester function, such as, for example, halo, 4-methylbenzenesulfonate, methanesulfonate and the like. Preferred reactive esters are halides and more particularly bromides and chlorides.

In one method of conducting the reaction between imidazole and (III), imidazole is first transformed into a metal salt thereof by treatment with an appropriate metallating agent such as, for example, a metal alkoxide, e.g., sodium- or potassium methanolate, or a metal hydride such as sodium hydride. The thus obtained metal salt is then reacted with (III) in an appropriate organic solvent, such as, for example, dimethylformamide or dimethylacetamide. A small amount of a metal iodide, such as sodium or potassium iodide may advantageously be added to promote the reaction, especially when the reactive ester is a chloride or bromide.

Alternatively, the reaction of imidazole with the reactive ester (III) may also be carried out without previous salt formation, by bringing the reactants into contact with each other in an appropriate organic solvent such as, for example, dimethylformamide or dimethylacetamide. In these circumstances it is appropriate to use an excess of imidazole or to add to the reaction mixture an appropriate base such as, for example, sodium or potassium carbonte or bicarbonate in order to bind the acid which is liberated during the course of the reaction. The use of an excess of imidazole is however preferred. Further it is advantageous to conduct the reaction in the presence of a metal iodide such as, for example, sodium or potassium iodide.

In each of the above procedures, somewhat elevated temperatures may be employed to enhance the rate of the reaction and most conveniently the reactions are carried out at the reflux temperture of the reaction mixture.

In these and the following preparations the reaction products may be isolated from the medium and, if necessary, further purified according to methodologies generally known in the art, such as, for example, extraction, trituration, crystallization, chromatography, etc..

The foregoing procedures are more fully illustrated by the following schematic representation:

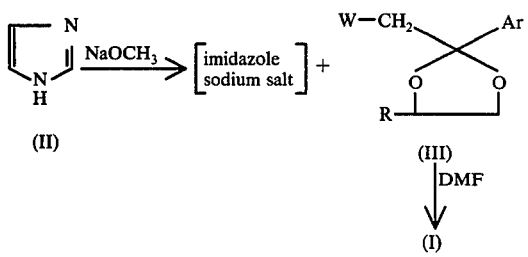

-continued

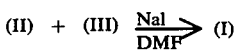

An additional method of preparing the compounds of formula (I) is by the ketalization of an appropriate aroylmethylimidazole of formula (IV) wherein Ar has the same meaning as assigned to it previously with an appropriate diol of formula (V) wherein R is as previously defined.

Said ketalization reaction may be carried out following methodologies analogous to those described in the literature, e.g., for the preparation of 2-bromomethyl-2,4-diphenyl-1,3-dioxolane [Synthesis, 1974 (I), 23].

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

The foregoing reaction may be illustrated as follows:

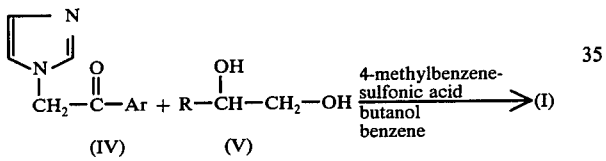

The compounds of formula (I) wherein R represents an alkyloxymethyl, alkenyloxymethyl, 2-propynyloxymethyl or arylmethoxymethyl radical, (I-a), may still by prepared by the reaction of an appropriate compound of formula (I) wherein R is hydroxymethyl (I-b) with an appropriate reactive ester of formula (VI) wherein $R^1$ is selected from the group consisting of alkyl, alkenyl, 2-propynyl and arylmethyl and W is a reactive ester function as previously defined, according to common O-alkylating procedures. Preferably the reaction is carried out in a suitable organic solvent such as, for example, dimethylformamide or dimethylacetamide in the presence of an appropriate strong metal base such as, for example, sodium hydride, sodium carbonate, potassium carbonate and the like.

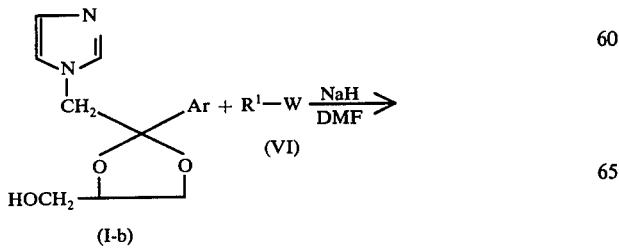

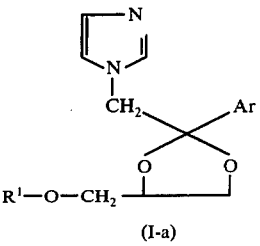

The compounds of formula (I) wherein R stands for alkyloxymethyl, (I-c), may still be prepared by the condensation of (I-b) with an appropriate alkanol. Said condensation reaction may be carried out by refluxing the reactants together under azeotropic water removal in an appropriate organic solvent such as, for example, an aromatic hydrocarbon, e.g., benzene, methylbenzene, dimethylbenzene and the like, a saturated hydrocarbon, e.g., cyclohexane, or in the alkanol itself, in the presence of an appropriate strong acid, such as, for example, 4-methylbenzenesulfonic acid.

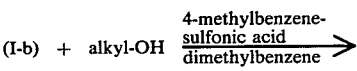

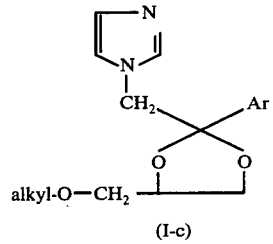

The compounds of formula (I-a) may still be prepared by the reaction of an appropriate reactive ester of formula (VII) wherein Ar and W are as defined hereinbefore with an appropriate hydroxy compound of the formula (VIII) wherein $R^1$ is as previously defined, according to common O-alkylating procedurs as described herebefore.

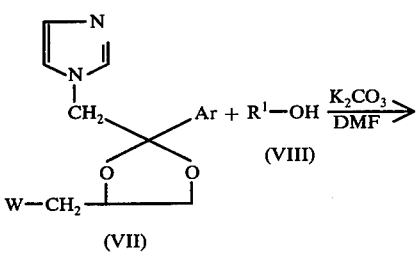

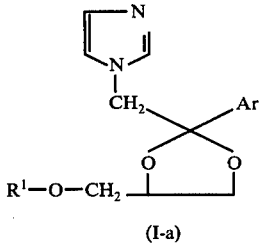

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, α-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propane-tricarboxylic, benzoic, 3-phenylpropenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

The intermediates of formula (III) may be prepared by subjecting an appropriate ketone of formula (IX), wherein Ar and W are as previously defined to a ketalization reaction with an appropriate diol of formula (V) in the same manner as described hereinbefore for the preparation of the compounds (I) starting from (IV) and (V).

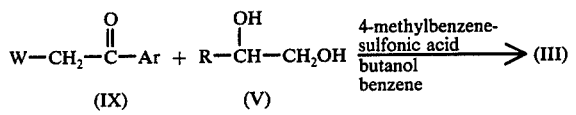

Alternatively the intermediates of formula (III) are conveniently prepared by transketalization of a ketal derivative of a ketone of formula (IX) such as, for example, a lower alkyl ketal or a cyclic lower alkylene ketal, with a glycol of formula (V) under conditions similar to those described hereinbefore for the direct ketalization. The lower alkyl ketals and cyclic lower alkylene ketals used herein as starting materials are easily obtained by ketalization of a ketone of formula (IX) with a lower alkanol or alkanediol according to methodologies known in the art. A number of such compounds and methods of preparing the same are described in U.S. Pat. Nos. 3,575,999 and 3,717,655.

The intermediates of formula (III) are deemed to be novel and as useful intermediates herein they constitute an additional feature of this invention.

A number of the precursor glycols of formula (V) are known and they may all be prepared according to known procedures as described in the literature. In general they may be derived from the corresponding 2-R-oxiranes of formula (X) by hydrolytic cleavage of the oxirane nucleus with an appropriate strong acid such as, for example, ethanedioic acid, sulfuric acid, hydrochloric acid and the like.

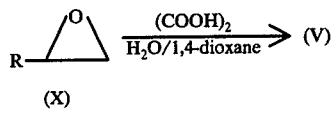

The oxiranes of formula (X) may in turn be obtained in a variety of ways.

Those of formula (X-a) wherein aryl is as previously defined may, for example, be prepared by oxidizing an appropriate 2-propenyl substituted arene of formula (XI) with an appropriate oxidizing agent such as, for example, a benzeneperoxoic acid, e.g., 3-chlorobenzeneperoxoic acid.

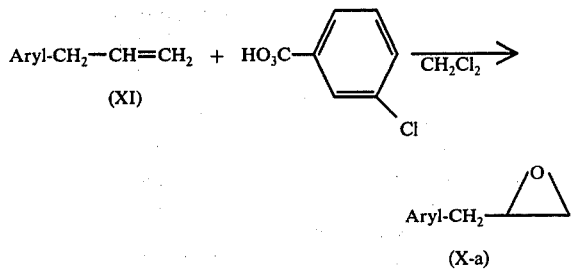

Those intermedites of formula (X) wherein R is alkyloxymethyl, alkenyloxymethyl, 2-propynyloxymethyl or arylmethoxymethyl, (X-b) are conveniently obtained by the reaction of an appropriate hydroxy compound of formula (VIII) wherein R¹ is alkyl, alkenyl, 2-propynyl or arylmethyl, with an appropriate 2-halomethyl oxirane of formula (XII) following common O-alkylating procedures as generally known in the art.

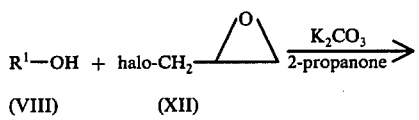

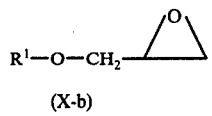

Intermediates of formula (V) wherein R stands for alkenyl may, for example, be prepared starting from an approprite hydroxyalkylsubstituted ethanediol by ketalizing the ethanediol group with an appropriate ketone, e.g., 2-propanone, converting thereafter the remaining hydroxy group on the alkyl chain into a methanesulfonate group by the reaction with methanesulfonyl chloride, splitting off methanesulfonic acid by treatment with an appropriate strong base such as, for example, sodium hydride in a suitable solvent such as dimethylformamide, and finally liberating the free diol from the ketal by treatment with an appropriate strong mineral acid such as, for example, hydrochloric or sulfuric acid.

In a preferred manner of carrying out the aforementioned reactions, the ketone used in the kelalization step is an intermediate of formula (IX) whereby the alkenyl-substituted dioxolanes of formula (III) are directly obtained in the course of the foregoing reaction sequence.

The precursor arylketones of formula (IX) are generally known and may be prepared according to known procedures as described in the literature. Bromides are, for example, easily obtained by the bromination of the corresponding methyl aryl methanone with bromine.

The aroylmethylsubstituted imidazoles of formula (IV), a number of which are described in U.S. Pat. Nos. 3,717,655 and 3,658,813, are conveniently prepared by the reaction of (IX) with imidazole in an analogous manner as previously described for the preparation of the compounds (I) starting from imidazole and (III).

The reactive esters of formula (VII), used as intermediates in the preparation of the compounds (I-a) are easily obtained by converting the corresponding alcohol of formula (I-b) into a reactive ester thereof according to methodologies generally known in the art. For example, methanesulfonates and 4-methylbenzenesulfonates are conveniently prepared by the reaction of the alcohol with respectively methanesulfonyl chloride or 4-methylbenzenesulfonyl chloride and halides may be prepared by the reaction of the alcohol with an appropriate halogenating agent such as, for example, sulfuryl chloride, phosphor pentachloride, phosphor pentabromide, phosphoryl chloride and the like. When the reactive ester is an iodide, it is preferably prepared from the corresponding chloride or bromide by the replacement of that halogen with iodine.

From formula (I) it is evident that the compounds of this invention have two asymmetric carbon atoms in their structures, namely those located in the 2- and 4-position of the dioxolane nucleus, and consequently they exist under different stereochemical optical isomeric forms. The stereochemical optical isomeric forms of (I) and the therapeutically active acid addition salts thereof are intended to be within the scope of this invention.

The diastereomeric racemates of (I), denoted as cis and trans forms respectively, according to the rules described in "Naming and Indexing of Chemical Substances for Chemical Abstracts during the 9th Collective Period (1972-1976)", published in C.A. 1972, 76, Index Guide Section IV, p. 85, may be obtained separately by conventional methods. Appropriate methods which may advantageously be employed therefore include, for example, selective crystallization and column-chromatography. For a number of compounds the stereochemical configuration was experimentally determined. In the remaining cases it is conventionally agreed to designate the sterochemical form which is first isolated as "A" and the second as "B", without further reference to the actual stereochemical configuration.

Since the asymmetric carbon atoms are already present in the intermediates (III) it is also possible to separate cis and trans forms, or generally "A" and "B" forms at this stage, whereupon the corresponding forms of (I) may be obtained after reaction of the foregoing with imidazole as previously described. The separation of cis and trans forms of (III) may be performed by conventional methods as described hereinbefore for the separation of the compounds (I) into their cis and trans forms. When R in the intermediates of formula (III) has the meaning of a hydroxymethyl group it may be advantageous to esterify first said hydroxymethyl group with an appropriate acylhalide, e.g., benzoyl chloride whereupon the thus obtained esters are separated into their cis and trans forms, from which the acyl group is subsequently split of hydrolytically in alkaline medium yielding the corresponding forms of the desired hydroxymethylsubstituted intermediates of formula (III).

It is evident that the cis and trans diastereomeric racemates may be further resolved into their optical isomers, cis (+), cis(−), trans (+) and trans (−) by the application of methodologies known to those skilled in the art.

The compounds of formula (I) and the acid addition salts thereof are useful agents in combatting fungi and bacteria. As such they are valuable in the treatment of human beings, animals and plants suffering from pathogenic microorganisms and in the destruction of microorganisms on materials. The broad spectrum of antifungal and antibacterial activity of the compounds of formula (I) is clearly illustrated by the experimental data presented hereafter. The compounds in the tables are not listed for the purpose of limiting the invention thereto, but only in order to exemplify the useful properties of all the compounds within the scope of formula (I).

the test for antifungal activity was performed using Sabouraud's liquid medium in test tubes each containing 4.5 ml of liquid medium, autoclaved at 120° C for 15 minutes. The substances were dissolved in 50% ethanol at a concentration of 20 mg/ml and subsequently diluted with sterile distilled water to a concentration of 10mg/ml. Successive decimal dilutions were then made with distilled water to give a series of stock solutions. To each tube containing 4.5 ml of Sabouraud's liquid medium was added 0.5 ml of one of the stock solutions to give a concentration of the drug under investigation of 100 μg, 10 μg, 1 μg or 0.1 μg per ml of medium. Filamentous fungi were incubated at 25° C for 2 - 3 weeks. A square block of side 2 mm. was excised and inoculated into the liquid medium. A three-day old culture on Sabouraud's liquid medium was used for yeasts, and the inoculum was 0.05 ml per tube. All the cultures were incubated at 25° C for 14 days. The final readings were taken after two weeks and are summarized in the Tables A as follows:

++++ = complete inhibition of growth at 0.1 μg/ml
+++ = complete inhibition of growth at 1 μg/ml
++ = complete inhibition of growth at 10 μg/ml
+ = complete inhibition of growth at 100 μg/ml
0 = no effect, i.e. growth was observed at the highest concentration tested (100 μg/ml).

In a first screening the drugs under investigation were tested against the following 11 fungi:
1. Microsporum canis (M.c. in the tables)
2. Ctenomyces mentagrophytes (Ct. m. in the tables)
3. Trichophyton rubrum (Tr. r. in the tables)
4. Phialophora verrucosa (Ph. v. in the tables)
5. Cryptococcus neoformans (Cr. n. in the tables)
6. Candida tropicalis (C. tr. in the tables)
7. Candida albicans (C. alb. in the tables)
8. Mucor species (Muc. in the tables)
9. Aspergillus fumigatus (A.f. in the tables)
10. Sporotrichum schenckii (Sp.s. in the tables)
11. Saprolegnia species (Sap. in the tables)

Bactericidal tests were performed on cultures on phenol red dextrose broth Difco medium. The same decimal dilution techniques as described herebefore were used. The inoculum consisted of a platinum loop (5 mm. diameter) from a 24 hour broth culture. 48 Hours after incubation, subcultures were made from each culture and for the assessment of the bactericidal activity of the drugs under investigation the presence or absence of growth after 7 days incubation was scored as described above.

The substances were tested against the following grampositive bacilli and cocci:
1. Erysipelothrix insidiosa (E. ins. in the table),
2. Staphylococcus hemolyticus (Staph. in the table), and
3. Streptococcus pyogenes (Strept. in the table).

The results are summarized in Tables B.

Tables A1
ANTIFUNGAL ACTIVITY

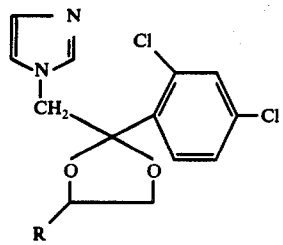

| R | Isomer | M.c. (1) | Ct.m. (2) | Tr.r. (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|
| ClCH$_2$ | A + B | +++ | +++ | +++ | ++ | ++ | + | 0 | + | +++ | +++ | ++ |
| ClCH$_2$ | cis | +++ | +++ | +++ | ++ | ++ | + | 0 | + | +++ | ++ | ++ |
| BrCH$_2$ | cis | +++ | +++ | +++ | ++ | +++ | + | ++ | 0 | +++ | ++ | ++ |
| CH$_2$=CH | A + B | +++ | +++ | +++ | + | ++ | + | + | + | +++ | + | ++ |
| CH$_2$=CH—CH$_2$—O—CH$_2$ | cis | ++ | +++ | +++ | + | +++ | + | 0 | + | ++ | ++ | ++ |
| CH≡C—CH$_2$—O—CH$_2$ | cis | ++ | +++ | +++ | + | +++ | + | 0 | 0 | + | + | + |
| CH≡C—CH$_2$—O—CH$_2$ | trans | + | + | ++ | + | 0 | 0 | 0 | 0 | + | + | + |

Tables A2
ANTIFUNGAL ACTIVITY

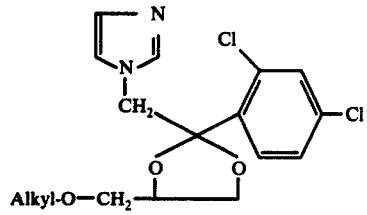

| Alkyl | isomer | M.c. (1) | Ct.m. (2) | Tr.r. (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|
| CH$_3$ | cis | ++ | +++ | +++ | ++ | ++ | ++ | 0 | 0 | ++ | + | ++ |
| C$_2$H$_5$ | trans | ++ | +++ | ++ | + | + | 0 | 0 | 0 | + | + | + |
| nC$_3$H$_7$ | cis | ++ | +++ | +++ | ++ | +++ | ++ | 0 | 0 | ++ | ++ | ++ |
| nC$_4$H$_9$ | A + B | ++ | +++ | +++ | + | ++ | + | + | + | + | ++ | ++ |
| nC$_5$H$_{11}$ | cis | ++ | +++ | +++ | + | +++ | ++ | 0 | ++ | ++ | ++ | ++ |
| nC$_6$H$_{13}$ | cis | ++ | +++ | +++ | + | +++ | ++ | 0 | + | + | ++ | + |
| nC$_7$H$_{15}$ | cis | + | +++ | +++ | + | +++ | 0 | 0 | + | + | ++ | + |
| nC$_8$H$_{17}$ | cis | + | +++ | +++ | + | +++ | 0 | 0 | + | 0 | ++ | 0 |
| C$_2$H$_5$ | cis | ++ | +++ | +++ | + | ++ | + | 0 | 0 | + | ++ | ++ |

Tables A3
ANTIFUNGAL ACTIVITY

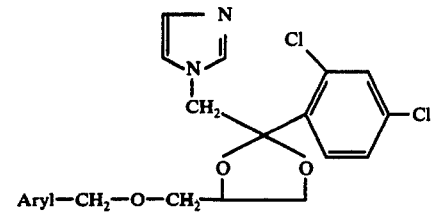

| Aryl | isomer | M.c. (1) | Ct.m. (2) | Tr.r. (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|
| 4-(C$_6$H$_5$)—C$_6$H$_4$ | cis | 0 | +++ | ++ | 0 | ++ | 0 | 0 | 0 | 0 | 0 | 0 |
| 4-(C$_6$H$_5$)—C$_6$H$_4$ | trans | 0 | +++ | + | 0 | 0 | 0 | 0 | 0 | 0 | 0 | 0 |
| 4-Br—C$_6$H$_4$ | cis | +++ | +++ | +++ | + | +++ | + | + | +++ | ++ | ++ | ++ |
| 2,4-(Cl)$_2$—C$_6$H$_3$ | cis | +++ | +++ | +++ | 0 | +++ | 0 | 0 | + | ++ | ++ | ++ |
| 2,4-(Cl)$_2$—C$_6$H$_3$ | trans | + | +++ | ++ | 0 | 0 | 0 | 0 | + | 0 | ++ | 0 |
| 4-Cl—C$_6$H$_4$— | cis | +++ | +++ | +++ | + | +++ | +++ | ++ | + | + | +++ | + |
| 4-F—C$_6$H$_4$— | cis | +++ | +++ | +++ | + | +++ | + | + | + | ++ | ++ | ++ |

Tables A4
ANTIFUNGAL ACTIVITY

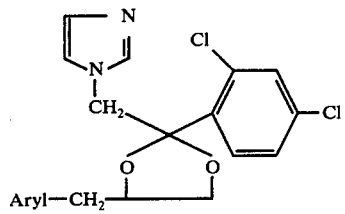

| Aryl | M.c. (1) | Ct.m. (2) | Tr.r. (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|
| $C_6H_5$ | +++ | +++ | +++ | + | +++ | ++ | + | ++ | +++ | ++ | ++ |
| 4-Cl—$C_6H_4$ | +++ | +++ | +++ | + | +++ | ++ | ++ | ++ | ++ | ++ | + |
| 4-F—$C_6H_4$ | +++ | +++ | +++ | + | +++ | ++ | + | +++ | ++ | ++ | ++ |
| 4-$CH_3$—$C_6H_4$ | +++ | +++ | +++ | + | +++ | 0 | ++ | ++ | ++ | ++ | ++ |
| 4-Br—$C_6H_4$ | +++ | +++ | +++ | + | +++ | 0 | ++ | +++ | ++ | ++ | + |
| 4-$OCH_3$—$C_6H_4$ | +++ | +++ | +++ | ++ | +++ | + | 0 | +++ | +++ | ++ | ++ |
| 4-($C_6H_5$)—$C_6H_4$ | ++ | +++ | +++ | 0 | + | 0 | 0 | 0 | ++ | + | + |

BACTERIOSTATIC AND BACTERIOCIDAL ACTIVITY
Table B

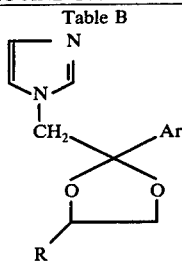

| Ar | R | Isomer | Bacteriostatic activity | | | Bacteriocidal activity | | |
|---|---|---|---|---|---|---|---|---|
| | | | E. ins. | Staph. | Strept. | E. ins. | Staph. | Strept. |
| 2,4-$(Cl)_2$—$C_6H_3$ | $CH_2Cl$ | A + B | + | 0 | + | + | 0 | + |
| 2,4-$(Cl)_2$—$C_6H_3$ | $CH_2OH$ | trans | + | 0 | + | 0 | 0 | + |
| 2,4-$(Cl)_2$—$C_6H_3$ | $CH_2OH$ | A + B | ++ | 0 | + | ++ | 0 | + |
| 2,4-$(Cl)_2$—$C_6H_3$ | $CH_2OH$ | cis | + | 0 | 0 | + | 0 | 0 |
| 2,4-$(Cl)_2$—$C_6H_3$ | $CH_2Cl$ | cis | ++ | 0 | 0 | ++ | 0 | 0 |
| 2,4-$(Cl)_2$—$C_6H_3$ | $CH_2Br$ | cis | +++ | ++ | ++ | +++ | + | 0 |
| 2,4-$(Cl)_2$—$C_6H_3$ | $CH=CH_2$ | A + B | +++ | + | ++ | +++ | 0 | + |
| 2,4-$(Cl)_2$—$C_6H_3$ | $CH_2$—O—$CH_2$—$CH=CH_2$ | cis | +++ | + | ++ | +++ | + | ++ |
| 2,4-$(Cl)_2$—$C_6H_3$ | $CH_2$—O—$CH_2$—$C\equiv CH$ | cis | ++ | + | ++ | ++ | + | ++ |
| 2,4-$(Cl)_2$—$C_6H_3$ | $CH_2$—O—$CH_2$—$C\equiv CH$ | trans | ++ | + | ++ | ++ | + | ++ |

| alkyl | isomer | Bacteriostatic activity | | | Bacteriocidal activity | | |
|---|---|---|---|---|---|---|---|
| | | E. ins. | Staph. | Strept. | E. ins. | Staph. | Strept. |
| $CH_3$ | cis | + | 0 | 0 | + | 0 | 0 |
| $C_2H_5$ | trans | ++ | + | ++ | + | 0 | + |
| $nC_3H_7$ | cis | ++ | + | + | ++ | 0 | 0 |
| $nC_4H_9$ | A+B | +++ | ++ | +++ | + | 0 | + |
| $nC_5H_{11}$ | cis | +++ | +++ | +++ | ++ | 0 | ++ |
| $nC_6H_{13}$ | cis | +++ | ++ | ++ | ++ | + | ++ |
| $nC_7H_{15}$ | cis | +++ | +++ | +++ | +++ | + | ++ |
| $nC_8H_{17}$ | cis | +++ | ++ | +++ | ++ | + | +++ |
| $C_2H_5$ | cis | ++ | + | ++ | ++ | 0 | 0 |

Bacteriostatic activity    Bacteriodical activity

-continued

| | | BACTERIOSTATIC AND BACTERIOCIDAL ACTIVITY | | | | | |
|---|---|---|---|---|---|---|---|
| Aryl | isomer | E. ins. | Staph. | Strept. | E. ins. | Staph. | Strept. |
| 4-($C_6H_5$)—$C_6H_4$ | cis | +++ | +++ | +++ | +++ | + | +++ |
| 4-($C_6H_5$)—$C_6H_4$ | trans | +++ | ++ | +++ | +++ | ++ | +++ |
| 4-Br—$C_6H_4$ | cis | +++ | ++ | +++ | +++ | + | +++ |
| 2,4-(Cl)$_2$—$C_6H_3$ | cis | +++ | +++ | +++ | ++ | + | ++ |
| 2,4-(Cl)$_2$—$C_6H_3$ | trans | +++ | ++ | +++ | +++ | + | ++ |
| 4-Cl—$C_6H_4$— | cis | +++ | ++ | ++ | +++ | + | ++ |
| 4-F—$C_6H_4$— | cis | +++ | ++ | +++ | +++ | + | +++ |

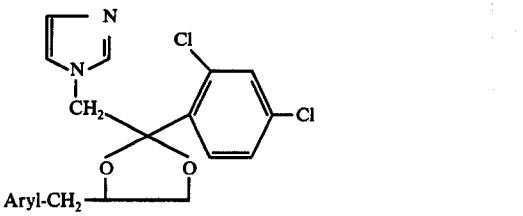

| | | Bacteriostatic activity | | | Bacteriocidal activity | |
|---|---|---|---|---|---|---|
| Aryl | E. ins. | Staph. | Strept. | E. ins. | Staph. | Strept. |
| $C_6H_5$ | +++ | ++ | ++ | +++ | + | ++ |
| 4-Cl—$C_6H_4$ | +++ | ++ | ++ | +++ | ++ | ++ |
| 4-F—$C_6H_4$ | +++ | ++ | ++ | ++ | + | ++ |
| 4-$CH_3$—$C_6H_4$ | +++ | ++ | +++ | +++ | ++ | +++ |
| 4-Br—$C_6H_4$ | +++ | ++ | +++ | +++ | ++ | +++ |
| 4-$OCH_3$—$C_6H_4$ | +++ | + | +++ | +++ | + | +++ |
| 4-($C_6H_5$)—$C_6H_4$ | +++ | ++ | +++ | ++ | + | ++ |

In view of the aforementioned antifungal and antibacterial activities this invention provides valuable compositions comprising the subject 1,3-dioxolan-2-ylmethyl imidazoles (I) or the acid addition salts thereof as the active ingredient in a solvent or a solid, semi-solid or liquid diluent or carrier, and, in addition, it provides an effective method of combatting fungus or bacterial growth by use of an effective anti-fungal or anti-bacterial amount of such ketals (I) or salts thereof. The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bacteridical effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetble origin are also suitable carrier substances.

The active ingredient is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings, Solvents suitable for this purpose are high-boiling oils, for example, of vegetable origin, and lower-boiling solvents with a flash point of at least 30° C., such as, for example, polyethylene glycols, isopropanol, dimethylsulfoxide, hydrogenated naphthalenes and alkylated naphthalenes. It is, of cours, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by fungi or bacteria.

The subject compounds and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, powder, ointment, emulsion, and the like forms, a high activity over a very high range of dilution is observed. For example, concentrations of the active ingredient ranging from 0.1 – 10 percent by weight, based on the weight of composition employed, have been found effective in combatting fungi or bacteria. Of course, higher concentrations may also be employed as warranted by the particular situation.

The following examples are intended to illustrate, but not to limit, the scope of the present invention. Unless otherwise stated, all parts are by weight.

EXAMPLE I

A mixture of 90 parts of 2-(4-bromophenylmethyl)oxirane, 8 parts of ethanedioic acid, 100 parts of water and 300 parts of 1,4-dioxane is stirred and refluxed overnight. The reaction mixture is evaporated. The residue is dissolved in trichloromethane. The solution is washed with 110 parts of a sodium hydroxide solution 10%, dried, filtered and evaporated. This The is distilled (bp. 165° C at 0.6 mm. pressure). The distillate is crystallized from 2,2′-oxybispropane. The product is filtered off and dried, yielding 25 parts of 3-(4-bromophenyl)-1,2-propanediol; mp. 60.6° C.

EXAMPLE II

Following the procedure of Example I, there is prepared 3-(4-fluorophenyl)-1,2-propanediol; bp. 125° C at 0.05 mm. pressure by hydrolyzing 2-(4-fluorophenylmethyl) oxirane.

EXAMPLE III

To a stirred mixture of 86 parts of 3-chlorobenzeneperoxoic acid and 650 parts of dichloromethane are added dropwise (slowly) 53 parts of 1-fluoro-4-(2-propenyl)benzene. Upon completion, stirring is continued overnight at room temperature. Then there are added dropwise 92 parts of a potassium carbonate solution and the layers are separated. The organic phase is washed with a sodium bisulfite solution, dried, filtered and evaporated, yielding 58.4 parts (98.5%) of 2-(4-fluorophenylemthyl)oxirane as an oily residue.

EXAMPLE IV

A mixture of 9.1 parts of 3-phenyl-1,2-propanediol, 15.2 parts of 2-bromo-1-(2,4-dichlorophenyl)ethanone, 3parts of 4-methylbenzenesulfonic acid, 40 parts of 1-butanol and 225 parts of dimethylbenzene is stirred and refluxed for 3 days with water-separator. The reaction mixture is cooled and 2,2′-oxybispropane is added. The whole is washed successively with a diluted sodium hydroxide solution and with water, dried, filtered and evaporated. The residue is dissolved in 2,2′-oxybispropane. The solution is stirred for 30 minutes with silica gel. The latter is filtered off and the filtrate is evaporated, yielding 27.2 parts of A + B-2-(bromomethyl)-2-(2,4-dichlorophenyl)-4-(phenylmethyl)-1,3-dioxolane as a residue.

EXAMPLE V

Following the procedure of example IV and using equivalent amounts of the appropriate starting materials, the following dioxolanes are still prepared:

A + B-2-(bromomethyl)-4-(4-chlorophenylmethyl)-2-(2,4-dichlorophenyl)-1,3-dioxolane as a residue;

A + B-2-(bromomethyl)-2-(2,4-dichlorophenyl)-4-(4-methoxyphenylmethyl)-1,3-dioxolane as a residue; and A + B-2-(bromomethyl)-2-(2,4-dichlorophenyl)-1,3-dioxolane-4-methanol; bp. 145°–150° C at 0.05 mm. pressure.

EXAMPLE VI

A. To a stirred mixture of 67.2 parts of A+B-2-(bromomethyl)-2-(2,4-dichlorophenyl)-1,3-dioxolane-4-methanol and 100 parts of pyridine are added dropwise 27.2 parts of benzoyl chloride while cooling at a temperature below 10° C. Upon completion, stirring is continued for 2.50 hours at room temperature. The reaction mixture is poured onto water and the product is extracted with trichloromethane. The extract is washed successively with a diluted hydrochloric acid solution, to remove the last traces of pyridine, and with water, dried filtered and evaporated. The oily residue is triturated in methanol. The solid product is filtered off (the filtrate is set aside) and crystallized twice from ethanol, yielding 28 parts of cis 2-(bromomethyl)-2-(2,4-dichlorophenyl)-1,3-dioxolan-4-ylmethyl benzoate; mp. 118.3° C. The filtrate (see above) is evaporated. The oily residue is purified by column-chromatography over silica gel using 2,2′-oxybispropane as eluent. The pure fractions are collected and the eluent is evaporated. The oily residue is triturated in methanol. The solid product is purified by column-chromatography over silica gel using trichloromethane and hexane (30:70) as eluent. The pure fractions are collected and the eluent is evaporated, yielding 17.5 parts of trans-2-(bromomethyl)-2-(2,4-dichlorophenyl)-1,3-dioxolan-4-ylmethyl benzoate; mp. 68.6° C.

B. A mixture of 12 parts of cis-2-(bromomethyl)-2-(2,4-dichlorophenyl)-1,3-dioxolan-4-ylmethyl benzoate, 7.5 parts of sodium hydroxide solution 60%, 100 parts of water and 200 parts of 1,4-dioxane is stirred and refluxed for 1 hour. The reaction mixture is cooled, poured onto water and the product is extracted with trichloromethane. The extract is washed with water, dried, filtered and evaporated. The oily residue is purified by column-chromatography over silica gel using a mixture of trichloromethane, hexane and methanol (50:49:1) as eluent. The pure fractions are collected and the eluent is evaporated, yielding 4.5 parts of cis-2-(bromomethyl)2-(2,4-dichlorophenyl)-1,3-dioxolane-4-methanol as a residue.

Following the procedure of Example VI-B and using an equivalent amount of trans-2-(bromomethyl)-2-(2,4-dichlorophenyl)-1,3-dioxolan-4-ylmethyl benzoate in place of the cis-2-(bromomethyl)-2-(2,4-dichlorophenyl)-1,3-dioxolan-4-ylmethyl benzoate, there is obtained: trans-2-(bromomethyl)-2-(2,4-dichlorophenyl)-1,3-dioxolane-4-methanol as a residue.

EXAMPLE VII

A mixture of 4.5 parts of methanesulfonyl chloride, 10 parts of cis-2-(2,4-dichlorophenyl)-2-(1H-imidazol-1-ylmethyl)-1,3-dioxolane-4-methanol and 50 parts of pyridine is allowed to stand for 3 hours at room temperature. The reaction mixture is poured onto water. The precipitated product is filtered off and crystallized from benzene, yielding 10.3 parts (87%) of cis-2-(2,4-dichlorophenyl)-2-(1H-imidazol-1-ylmethyl)-1,3-dioxolan-4-ylmethyl methanesulfonate; mp. 111.7° C.

EXAMPLE VIII

A mixture of 32 parts of 1,2,4-butanetriol, 60 parts of 2-bromo-1-(2,4-dichlorophenyl)ethanone, 2 parts of 4-methylbenzenesulfonic acid, 40 parts of butanol and 225 parts of methylbenzene is stirred and refluxed overnight with water-separator. The reaction mixture is cooled, washed with a potassium carbonate solution, dried, filtered and evaporated. The residue is purified by column-chromatography over silica gel using a mixture of trichloromethane and methanol (99:1) as eluent. The pure fractions are collected and the eluent is evaporated, yielding 34 parts (43%) of A+B-2-(bromomethyl)-2-(2,4-dichlorophenyl)-1,3-dioxolane-4-ethanol as a residue.

To a stirred mixture of 20 parts of A+B-2-(bromomethyl)-2-(2,4-dichlorohenyl)-1,3-dioxolane-4-ethanol and 50 parts of pyridine are added dropwise 6.9 parts of methanesulfonyl chloride. Upon completion, stirring at room temperature is continued for 2 hours. The reaction mixture is poured onto water and the product is extracted twice with 1,1'-oxybisethane. The combined extracts are washed successively twice with a diluted hydrochloric acid solution and once with water, dried, filtered and evaporated, yielding 25 parts (100%) of A+B-{2-[2-(bromomethyl)-2-(2,4-dichlorophenyl)-1,3-dioxolan-4-yl]ethyl} methanesulfonate as a residue.

To a stirred mixture of 25 parts of A+B-{2-[2-(bromomethyl)-2-(2,4-dichlorophenyl)-1,3-dioxolan-4-yl]ethyl} methanesulfonate and 100 parts of dimethylsulfoxide are added 2.2 parts of sodium hydride dispersion 78% at room temperature. Stirring is continued for 3 hours at 50° C. The reaction mixture is poured onto water and the product is extracted twice with 2,2'-oxybispropane. The combined extracts are washed twice with water, dried, filtered and evaporated. The residue is purified by columnchromatography over silica gel using trichloromethane as eluent. The pure fractions are collected and the eluent is evaporated, yielding 15 parts (79%) of A+B-2-(bromomethyl)-2-(2,4-dichlorophenyl)-4-ethenyl-1,3-dioxolane as a residue.

EXAMPLE IX

A mixture of 17 parts of 1H-imidazole, 27.2 parts of A + B-2-(bromomethyl)-2-(2,4-dichlorophenyl-4-(phenylmethyl)1,3-dioxolane and 135 parts of N,N-dimethylacetamide is stirred and refluxed for 3 days. The reaction mixture is allowed to cool to room temperature and poured onto water. The product is extracted twice with 1,1'-oxybisethane. The combined extracts are washed with water, dried, filtered and evaporated. The residue is converted into the ethanedioate salt in 4-methyl-2-pentanone and 2,2'-oxybispropane. The salt is filtered off and crystallized from a mixture of acetonitrile and 2,2'-oxybispropane, yielding 17.2 parts (60%) of A +B-1-[2,4-dichlorophenyl)-4-(phenylmethyl)-1,3-dioxolan-2-ylmethyl]-1H-imidazole diethanedioate; mp. 117.1° C.

EXAMPLE X

Following the procedure of example IX and using equivalent amounts of the appropriate starting materials, there are prepared:

A + B-1-[4-(4-chlorophenylmethyl)-2-(2,4-dichlorophenyl)-1,3-dioxolan2-ylmethyl]-1H-imidazole sesquiethanedioate; mp. 141.6° C: and A + B-1-[2-(2,4-dichlorophenyl)-4-(4-methoxyphenylmethyl)-1,3-dioxolan-2- ylmethyl]-1H -imidazole diethanedioate; mp. 94.2° C.

EXAMPLE XI

A mixture of 32 parts of 1-(2,4-dichlorophenyl)-2-(1H-imidazol-1-yl)ethanone, 55 parts of 1,2,3-propanetriol, 35 parts of 4-methylbenzenesulfonic acid, 96 parts of butanol and 360 parts of dimethylbenzene is stirred and refluxed for 5 days with water-separator. The reaction mixture is cooled, washed with a potassium carbonate solution and with water, dried, filtered and evaporated. The residue is dissolved in a diluted ethanedioic acid solution. The resulting solution is washed twice with 1,1'-oxybisethane. The aqueous phase is separated and neutralized with potassium carbonate. The product is extracted with trichloromethane. The extract is dried, filtered and evaporated. The residue is purified by column-chromatography over silica gel using a mixture of trichloromethane and 2% of methanol as eluent. The first fraction is collected and the eluent is evaporated. The residue is converted into the nitrate salt in 2,2'-oxybispropane. The salt is filtered off and crystallized from a mixture of 4-methyl-2-pentanone and 2,2'-oxybispropane, yielding 5.5 parts (9.8%) of A+B-1-[4-(butoxymethyl)-2-(2,4-dichlorophenyl)-1,3-dioxolan-2-ylmethyl]-1H-imidazole nitrate; mp. 101.8° C. The second fraction is collected and the eluent is evaporated. The residue is triturated in 1,1'-oxybisethane. The product is filtered off and crystallized from a mixture of 4-methyl-2-pentanone and petroleumether, yielding 9.75 parts of A+B-2-(2,4-dichlorophenyl)-2-(1H-imidazol-1-ylmethyl)-1,3-dioxolane-4-methanol; mp. 128.1° C.

EXAMPLE XII

A mixture of 7.7 parts of 1H-imidazole, 8 parts of cis-2-(bromomethyl)-2-(2,4-dichlorophenyl)-1,3-dioxolane-4-methanol, 1 part of potassium iodide and 180 parts of N,N-dimethylacetamide is stirred and refluxed for 3 days. The reaction mixture is cooled and evaporated. Then there are added 50 parts of water and 300 parts of trichloromethane to the residue. The whole is washed three times with water, dried, filtered and evaporated. The residue is purified by column-chromatography over silica gel using a mixture of trichloromethane and 2% of methanol as eluent. The pure fractions are collected and the eluent is evaporated, yielding 9.2 parts of cis-2-(2,4-dichlorophenyl)-2-(1H-imidazol-1-ylmethyl)-1,3-dioxolane-4-methanol; mp. 140° C.

EXAMPLE XIII

Following the procedure of Example XII and using an equivalent amount of trans-2-(bromomethyl)-2-(2,4-dichlorophenyl)-1,3-dioxolane-4-methanol as a starting material, there is obtained: trans-2-(2,4-dichlorophenyl)-2-(1H-imidazol-1-ylmethyl)-1,3-dioxolane-4-methanol; mp. 129° C.

EXAMPLE XIV

To a stirred mixture of 4parts of cis-2-(2,4-dichlorphenyl)-2-(1H-imidazol-1-ylmethyl)-1,3-dioxolane-4-methanol, 2.2 parts of iodomethane and 90 parts of N,N-dimethylformamide are added 0.5 parts of sodium hydride dispersion 78%. Stirring is continued for 2 hours at room temperature. The reaction mixture is poured onto water and the product is extracted three times with 1,1'-oxybisethane. The combined extracts are washed with water and acidified with a nitric acid solution in 1,1'-oxybisethane. The formed nitrate salt is filtered off and crystallized from 4-methyl-2-pentanone, yielding 2.2 parts (45%) of cis-1-[2-(2,4-dichlorophenyl)-4-(methoxymethyl)-1,3-dioxolan-2-ylmethyl]-1H-imidazole nitrate; mp. 140° C.

EXAMPLE XV

To a stirred mixture of 4 parts of cis-2-(2,4-dichlorophenyl)-2-(1H-imidazol-1-ylmethyl)-1,3-dioxolane-4-methanol, 1.7 parts of bromethane and 90 parts of N.N-dimethylformamide are added 0.5 parts of sodium hydride dispersion 78%. The whole is stirred for 1 hour at room temperature. The reaction mixture is poured onto water and the product is extracted three times with 2,2'-oxybispropane. The combined extracts are washed with water and acidified with a nitric acid solution in 2,2'-oxybispropane. The formed nitrate salt is filtered off and crystallized from a mixture of 4-methyl-2-pentanone and 2,2'-oxybispropane, yielding 4.7 parts (93%) of cis-1-[2-(2,4-dichlorophenyl)-4-(ethoxymethyl)-1,3-dioxolan-2-ylmethyl]-1H-imidazole nitrate; mp. 134.7° C.

EXAMPLE XVI

Following the procedure of Example XV and using an equivalent amount of an appropriate bromoalkane or bromoalkene in place of the bromoethane used therein, the following imidazole acid addition salts are prepared:
 cis-1-[2-(2,4-dichlorophenyl)-4-propoxymethyl)-1,3-dioxolan-2-ylmethyl]-1H-imidazole nitrate; mp. 131.7° C;
 cis-1-[2-(2,4-dichlorophenyl)-4-(pentyloxymethyl)-1,3-dioxolan-2-ylmethyl]-1H-imidazole nitrate; mp. 78.6° C;
 cis-1-[2-(2,4-dichlorophenyl)-4-(hexyloxymethyl)-1,3-dioxolan-2-ylmethyl]-1H-imidazole nitrate; mp. 87.1° C;
 cis-1-[2-(2,4-dichlorophenyl)-4-(heptyloxymethyl)-1,3-dioxolan-2-ylmethyl]-1H-imidazole nitrate; mp. 80.7° C; and
 cis-1-[2-(2,4-dichlorophenyl)-4-octyloxymethyl)-1,3-dioxolan-2-ylmethyl]-1H-imidazole nitrate; mp. 73.4° C.

EXAMPLE XVII

To a stirred mixture of 1.8 parts of 3-bromo-1-propene, 4parts of cis-2-(2,4-dichlorophenyl)-2-(1H-imidazol-1-ylmethyl)-1,3-dioxolane-4-methanol and 90 parts of N,N-dimethylformamide are added 0.5 parts of a sodium hydride dispersion 78%. The whole is stirred for 3 hours at room temperature. The reaction mixture is poured onto water and the product is extracted twice with 2,2'-oxybispropane. The combined extracts are washed with water and acidified with a nitric acid solution in 2,2'-oxybispropane. The formed nitrate salt is filtered off and crystallized from a mixture of 4-methyl-2-pentanone and 2,2'-oxybispropane, yielding 3.4 parts (65%) of cis-1-[2-(2,4-dichlorophenyl)-4-(2-propenyloxymethyl)-1,3-dioxolan-2-ylmethyl]-1H-imidazole nitrate; mp. 116.3° C.

EXAMPLE XVIII

To a mixture of 4 parts of trans-2-(2,4-dichlorophenyl)-2-(1H-imidazol-1-ylmethyl)-1,3-dioxolane-4-methanol, 1.7 parts of bromoethane and 90 parts of N.N-dimethylformamide are added 0.5 parts of sodium hydride dispersion 78% and the whole is stirred for 2 hours at room temperature. The reaction mixture is poured onto water and the product is extracted twice with 2,2'-oxybispropane. The combined extracts are washed with water and taken up in 2,2'-oxybispropane. The solution is acidified with nitric acid. The formed nitrate salt is filtered off and crystallized from 4-methyl-2-pentanone, yielding 3.5 parts (69%) of trans-1-[2-(2,4-dichlorophenyl)-4-ethoxymethyl)-1,3-dioxolan-2-ylmethyl]-1H-imidazole nitrate; mp. 151.4° C.

EXAMPLE XIX

To a stirred mixture of 2.5 parts of 1-chloro-4-(chloromethyl)benzene, 4 parts of cis-2-(2,4-dichlorophenyl)-2-(1H-imidazol-1-ylmethyl)-1,3-dioxolane-4-methanol and 90 parts of N.N-dimethylformamide are added 0.5 parts of sodium hydride dispersion 78%. Stirring is continued for 5 hours at room temperature. The reaction mixture is poured onto water and the product is extracted twice with 2,2'-oxybispropane. The combined extracts are washed with water, dried, filtered and acidified with nitric acid. The formed nitrate salt is filtered off and crystallized from a mixture of 4-methyl-2-pentanone and 2,2'-oxybispropane. The product is filtered off and recrystallized from a mixture of 4-methyl-2-pentanone and 2,2'-oxybispropane, yielding 3.5 parts (56%) of cis-1-[4-(4-chlorophenylmethoxymethyl)-2-(2,4-dichlorophenyl)-1,3-dioxolan-2-ylmethyl]-1H-imidazole nitrate; mp. 131.7° C.

EXAMPLE XX

Following the procedure of Example XIX and using an equivalent amount of an appropriate (chloromethyl)benzene in place of the 1-chloro-4-(chloromethyl)benzene used therein, there are obtained:
 cis-1-{4-[(4-bromophenyl)methoxymethyl]-2-(2,4-dichlorophenyl)-1,3-dioxolan-2-ylmethyl}-1H-imidazole nitrate; mp. 101.4° C; and
 cis-1-{2-(2,4-dichlorophenyl)-4-[(4-fluorophenyl)methoxymethyl]-1,3-dioxolan-2-ylmethyl}-1H-imidazole nitrate; mp. 107° C.

EXAMPLE XXI

To a stirred mixture of 3,3 parts of 2,4-dichloro-1-(chloromethyl)benzene, 5 parts of A+B-2-(2,4-dichlorophenyl)-2-(1H-imidazol-1-ylmethyl)-1,3-dioxolane-4-methanol and 90 parts of N,N-dimethylformamide are added 0.5 parts of sodium hydride dispersion 78% and stirring is continued for 3 hours at room temperature. The reaction mixture is poured onto water and the product is extracted three times with 2,2'-oxybispropane. The combined extracts are washed with water, dried, filtered and evaporated. The residue is purified by column-chromatography over silica gel using trichlormethane as eluent. The first frction (A-isomer) is collected and the eluent is evaporated. The residue is converted into the nitrate salt in 4-methyl2-pentanone and 2,2'-oxybispropane. The salt is filtered off and recrystallized from a mixture of 4-methyl-2-pentanone and 2,2'-oxybispropane at 0° C, yielding 2.9 parts (35%) of cis-1-{2-(2,4-dichlorophenyl)-4-[(2,4-dichlorophenyl)methoxyumethyl]-1,3-dioxolan-2-ylmethyl}-1H-imidazole nitrate; mp. 96.9° C. The second fraction (B-isomer) is collected and the eluent is evaporated. The residue is converted into the nitrate salt in 4-methyl-2-pentanone and 1,1'-oxybisethane. The salt is filtered off and recrystallized from a mixture of 4-methyl-2-pentanone and 2,2'-oxybispropane, yielding 1.6 parts (19%) of trans-1-{2-(2,4-dichlorophenyl)-4-[(2,4- dichlorophenyl)methoxymethyl]-1,3-dioxolan-2-ylmethyl}-1H-imidazole nitrate; mp. 131.9° C.

EXAMPLE XXII

By repeating the procedure of Example XXI and using an equivalent amount of 4-(chloromethyl)-1,1'-biphenyl in place of the 2,4-dichloro-1-chloromethylbenzene used therein, there are obtained: cis-1-[4-([1,1'-biphenyl]-4-ylmethoxymethyl)-2-(2,4-dichlorophenyl)-1,3-dioxolan-2-ylmethyl]-1H-imidazole diethanedioate; mp. 107.6° C; and trans-1-[4-([1,1'-biphenyl]-4-ylmethoxymethyl)-2-(2,4-dichlorophenyl)-1,3-dioxolan-2-ylmethyl]-1H-imidazole nitrate; mp. 168° C.

EXAMPLE XXIII

A mixture of 13.7 parts of 3-([1,1'-biphenyl]-4-yloxy)-1,2-propanediol, 12.8 parts of 1-(2,4-dichlorophenyl)-2-(1H-imidazol-1-yl)ethanone, 16 parts of 4-methylbenzenesulfonic acid, 40 parts of 1-butanol and 225 parts of dimethylbenzene is stirred and refluxed for 7 days with water-separator. The reaction mixture is cooled and diluted with 1,1'-oxybisethane. The organic phase is washed with a diluted sodium hydroxide solution and with water, dried, filtered and evaporated. The residue is converted into the ethanedioate salt in 4-methyl-2-pentanone and 2,2'-oxybispropane. The salt is filtered off and crystallized from 4-methyl-2-pentanone, yielding 12.8 parts (39%) of A + B-1-[4-([1,1'-biphenyl]-4-ylmethyl)-2-(2,4-dichlorophenyl)-1,3-dioxolan-2-ylmethyl]-1H-imidazole diethanedioate; mp. 116.8° C..

EXAMPLE XXIV

Following the procedure of Example XXIII and using equivalent amounts of the appropriate starting materials, the following imidazole acid addition salts are prepared:

A + B-1-[4-(chloromethyl)-2-(2,4-dichlorophenyl)-1,3-dioxolan-2-ylmethyl]-1H-imidazole nitrate; mp. 166.1° C;

cis-1-[4-(bromomethyl)-2-(2,4-dichlorophenyl)-1,3-dioxolan-2-ylmethyl]-1H-imidazole nitrate; mp. 159.9° C;

A + B-1-[2-(2,4-dichlorophenyl)-4-(4-fluorophenylmethyl)-1,3-dioxolan-2-ylmethyl]-1H-imidazole sesquiethanedioate; mp. 153.1° C;

A + B-1-{2-(2,4-dichlorophenyl)-4-[(4-methylphenyl)methyl]-1,3-dioxolan-2-ylmethyl}-1H-imidazole sesquiethanedioate; mp. 123.1° C; and A + B-1-[4-(4-bromophenylmethyl)-2-(2,4-dichlorophenyl)-1,3-dioxolan-2-ylmethyl]-1H-imidazole diethanedioate; mp. 128.8° C.

EXAMPLE XXV

To a stirred mixture of 1.1 parts of 3-chloro-1-propyne, 4 parts of cis-2-(2,4-dichlorophenyl)-2-(1H-imidazol-1-ylmethyl)-1,3-dioxolane-4-methanol and 90 parts of N,N-dimethylformamide are added 0.5 parts of sodium hydride dispersion 78%. Stirring is continued for 3 hours at room temperature. The reaction mixture is poured onto water and the product is extracted twice with 1,1'-oxybisethane. The combined extracts are washed with water, dried, filtered and evaporated. The residue is purified by column-chromatography over silica gel using a mixture of trichloromethane and methanol (98:2) as eluent. The pure fractions are collected and the eluent is evaporated. The residue is converted into the ethanedioate salt in 4-methyl-2-pentanone and 2,2'-oxybispropane. The salt is filtered off and crystallized from 4-methyl-2-pentanone, yielding 3.6 parts (55%) of cis-1-[2-(2,4-dichlorophenyl)-4-(2-propynyloxymethyl)-1,3-dioxolan-2-ylmethyl]-1H-imidazole diethanedioate; mp. 145.6° C.

EXAMPLE XXVI

A mixture of 17 parts of 1H-imidazole, 16 parts of A + B-2-(bromomethyl)-2-(2,4-dichlorophenyl)-4-ethenyl-1,3-dioxolane and 225 parts of N,N-dimethylformamide is stirred and refluxed for 3 days. The reaction mixture is cooled, poured onto water and the product is extracted twice with 1,1'-oxybisethane. The combined extracts are washed with water, dried, filtered and evaporated. The residue is purified by column-chromatography over silica gel using trichloromethane as eluent. The pure fractions are collected and the eluent is evaporated. The residue is converted into the nitrate salt in 4-methyl-2-pentanone and 2,2'-oxybispropane. The salt is filtered off and crystallized from 4-methyl-2-pentanone, yielding 2.4 parts (13%) of A + B-1-[2-(2,4-dichlorophenyl)-4-ethenyl)-1,3-dioxolan-2-ylmethyl]-1H-imidazole nitrate; mp. 150.9° C.

EXAMPLE XXVII

A mixture of 48 parts of sulfinyl chloride and 2 parts of cis-2-(2,4-dichlorophenyl)-2-(1H-imidazol-1-ylmethyl)-1,3-dioxolane-4-methanol is stirred and refluxed for one hour. The reaction mixture is evaporated. The residue is treated with a sodium hydrogen carbonate solution and the product is extracted with 105 parts of 2,2'-oxybispropane. The extract is dried, filtered and evaporated. The residue is converted into the nitrate salt in 2,2'-oxybispropane. The salt is filtered off and crystallized from 2-propanol, yielding 2.1 parts (85%) of cis-1-[4-(chloromethyl)- 2-(2,4-dichlorophenyl)-1,3-dioxolan-2-ylmethyl]-1H-imidazole nitrate; mp. 181.2° C.

EXAMPLE XXVIII

To a stirred mixture of 115 parts of 3-chloropropyne, 400 parts of cis-2-(2,4-dichlorophenyl)-2-(1H-imidazol-1-ylmethyl)-1,3-dioxolane-4-methanol and 7200 parts of N,N-dimethylformamide are added portionwise 50 parts of a sodium hydride dispersion 78% while stirring is continued vigorously. Upon completion, stirring is continued for 4 hours. The reaction mixture is poured onto 20,000 parts of water and the whole is evaporated. The residue is decomposed with methanol while nitrogen gas is introduced. After stirring for 20 minutes, the product is extracted with 2,2'-oxybispropane. The extract is dried, filtered and evaporated. The residue is purified by column-chromatography over silica gel using a mixture of trichloromethane, hexane and ethanol (50:50:10 by volume) as eluent. The pure fractions are collected and the eluent is evaporated. The residue is converted into the hydrochloride salt in hexane and 2-propanol. The salt is filtered off, stirred in 2-propanone and dried overnight at 50° C, yielding 184 parts (37.6%) of cis-1-{2-(2,4-dichlorophenyl)-4-[(2-propynyloxy)methyl]-1,3-dioxolan-2-ylmethyl}-1H-imidazole monohydrochloride; mp. 172.6° C.

EXAMPLE XXIX

A mixture of 2.2 parts of 3-bromo-1-propyne, 6 parts of trans-2-(2,4-dichlorophenyl)-2-(1H-imidazol-1-ylmethyl)-1,3-dioxolane-4-methanol and 90 parts of N,N-dimethylformamide is stirred and cooled in an ice-bath while nitrogen gas is introduced. Then there are added 0.6 parts of a sodium hydride dispersion 78% and stirring is continued for 3 hours at room temperature. The reaction mixture is poured onto water and the product is extracted twice with 2,2'-oxybispropane. The combined extracts are washed with water, dried, filtered and evaporated. The residue is converted into the nitrate salt in 1,1'-oxybisethane. The salt is filtered off and crystallized from 4-methyl-2-pentanone, yielding 4.7 parts (60%) of trans-1-[2-(2,4-dichlorophenyl)-4-(2-propynyloxymethyl)-1,3-dioxolan-2-ylmethyl]-1H-imidazole mononitrate; mp. 116.1° C.

EXAMPLE XXX

Following the procedure of Example XXIII and using equivalent amounts of the appropriate starting materials, the following imidazoles are prepared:
1-[2-(4-chlorophenyl)-4-(phenylmethyl)-1,3-dioxolan-2-ylmethyl]-1H-imidazole;
1-[4-(2,4-dichlorophenylmethyl)-2-(4-methylphenyl)-1,3-dioxolan-2-ylmethyl]-1H-imidazole;
1-[4-(2,4-dichlorophenylmethyl)-2-(4-methoxyphenyl)-1,3-dioxolan-2-ylmethyl]-1H-imidazole;
1-[2-(4-nitrophenyl)-4-(phenylmethyl)-1,3-dioxolan-2-ylmethyl]-1H-imidazole;
4-[2-(1H-imidazol-1-ylmethyl)-4-(phenylmethyl)-1,3-dioxolan-2-yl]-benzonitrile;
1-{4-[(4-fluorophenyl)methyl]-2-(2-thienyl)-1,3-dioxolan-2-ylmethyl}-1H-imidazole;
1-{2-(5-chloro-2-thienyl)-4-[(4-methylphenyl)]-1,3-dioxolan-2-ylmethyl}-1H-imidazole; and
1-{4-[(4-bromophenyl)methyl]-2-(2-naphthalenyl)-1,3-dioxolan-2-ylmethyl}-1H-imidazole.

EXAMPLE XXXI

Following the procedure of Example XI and using equivalent amounts of the appropriate starting materials, the following 2-aryl-2-(1H-imidazol-1-ylmethyl)-1,3-dioxolane-4-methanols are prepared:
2-(4-chlorophenyl)-2-(1H-imidazol-1-ylmethyl)-1,3-dioxolane-4-methanol;
2-(1H-imidazol-1-ylmethyl)-2-(4-methylphenyl)-1,3-dioxolane-4-methanol;
2-(1H-imidazol-1-ylmethyl)-2-(4-methoxyphenyl)-1,3-dioxolane-4-methanol;
2-(1H-imidazol-1-ylmethyl)-2-(4-nitrophenyl)-1,3-dioxolane-4-methanol;
4-[2-(1H-imidazol-1-ylmethyl)-4-(hydroxymethyl)-1,3-dioxolan-4-yl]benzonitrile;
2-(1H-imidazol-1-ylmethyl)-2-(2-thienyl)-1,3-dioxolane-4-methanol;
2-(5-chloro-2-thienyl)-2-(1H-imidazol-1-ylmethyl)-1,3-dioxolane-4-methanol; and
2-(1H-imidazol-1ylmethyl)-2-(2naphthalenyl)-1,3-dioxolane-4-methanol.

EXAMPLE XXXII

Following the procedure of Example XXVIII and using equivalent amounts of the appropriate starting materials, there are prepared:
1-[2-(4-chlorophenyl)-4-(2-propynyloxymethyl)-1,3-dioxolan-2-ylmethyl]-1H-imidazole;
1-[2-(4-methylphenyl)-4-(2-propynyloxymethyl)-1,3-dioxolan-2-ylmethyl]-1H-imidazole;
1-[2-(4-methoxyphenyl)-4-(2-propynyloxymethyl)-1,3-dioxolan-2-ylmethyl]-1H-imidazole;
1-[2-(4-nitrophenyl)-4-(2-propynyloxymethyl)-1,3-dioxolan-2-ylmethyl]-1H-imidazole;
4-[2-(1H-imidazol-1-yl)-4-(2-propynyloxymethyl)-1,3-dioxolan-2-ylmethyl]-benzonitrile.
1-[4-(2-propynyloxymethyl)-2-(2-thienyl)-1,3-dioxolan-2-ylmethyl]-1H-imidazole;
1-[2-(5-chloro-2-thienyl)-4-(2-propynyloxymethyl)-1,3-dioxolan-2-ylmethyl]-1H-imidazole;
1-[2-(2-naphthalenyl)-4-(2-propynyloxymethyl)-1,3-dioxolan-2-ylmethyl]-1H-imidazole;
1-[2-(4-chlorophenyl)-4-(2-propenyloxymethyl)-1,3-dioxolan-2-ylmethyl]-1H-imidazole;
1-[2-(4-methylphenyl)-4-(2-propenyloxymethyl)-1,3-dioxolan-2-ylmethyl]-1H-imidazole;
1-[2-(4-nitrophenyl)-4-(2-propenyloxymethyl)-1,3-dioxolan-2-ylmethyl]-1H-imidazole;
4-[2-(1H-imidazol-1-ylmethyl)-4-(2-propenyloxymethyl)-1,3-dioxolan-2-yl]benzonitrile;
1-[2-(4-chlorophenyl)-4-(phenylmethoxymethyl)-1,3-dioxolan-2-ylmethyl]-1H-imidazole; and
1-{2-(4-chlorophenyl)-4-[(4-chlorophenyl)methoxymethyl]-1,3-dioxolan-2-ylmethyl}-1H-imidazole.
1-[2-(2,4-dichlorophenyl)-4-(2-propenyloxymethyl)-1,3-dioxolan-2-ylemthyl-1 H-imidazole; and
1- 2-(2,4-dichlorophenyl)-4-[(2-propynyloxy)methyl]-1,3-dioxolan-2-ylmethyl-1H-imidazole.

I claim:
1. A chemical compound selected from the group consisting of an imidazole derivative having the formula:

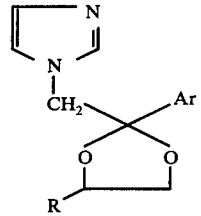

and the therapeutically acceptable acid addition salts and stereochemical optical isomeric forms thereof, wherein:
Ar is a member selected from the group consisting of phenyl, substituted phenyl, thienyl, halothienyl and naphthalenyl, and wherein said substituted phenyl is phenyl having from 1 to 3 substituents independently selected from the group consisting of halo, lower alkyl, lower alkyloxy, nitro and cyano; and
R is a member selected from the group consisting of alkyloxymethyl wherein the alkylgroup has from 1 to 10 carbon atoms, alkenyl, alkenyloxymethyl, wherein said alkenyl has from 2 to 10 carbon atoms, hydroxymethyl, 2-propynyloxymethyl, halomethyl, arylmethyl and arylmethoxymethyl, wherein said aryl is a member selected from the group consisting of phenyl, substituted phenyl, naphthalenyl and mono- and di-halonaphthalenyl, and wherein said substituted phenyl is phenyl having from 1 to 3 substituents independently selected from the group consisting of halo, lower alkyl, lower alkyloxy, cyano, nitro, phenyl, phenylmethyl, benzoyl, halobenzoyl, lower alkylcarbonyl, lower alkyloxycarbonyl and trifluoromethyl, provided that when more than 1 substituents are present only 1 thereof may be selected from the group consisting of phenyl, phenylmethyl, benzoyl and halobenzoyl.

2. A chemical compound selected from the group consisting of an imidazole derivative having the formula:

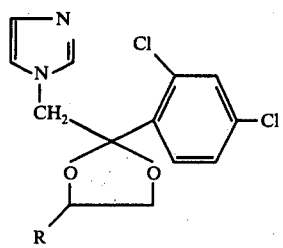

and the therapeutically acceptable acid addition salts and stereochemical optical isomeric forms thereof, wherein:

R is a member selected from the group consisting of alkyloxymethyl wherein the alkylgroup has from 1 to 10 carbon atoms, alkenyl, alkenyloxymethyl, wherein said alkenyl has from 2 to 10 carbon atoms, hydroxymethyl, 2-propynyloxymethyl, halomethyl, arylmethyl and arylmethoxymethyl, wherein said aryl is a member selected from the group consisting of phenyl, substituted phenyl, naphthalenyl wnd mono- and di-halonaphthalenyl, and wherein said substituted phenyl is phenyl having from 1 to 3 substituents independently selected from the group consisting of halo, lower alkyl, lower alkyloxy, cyano, nitro, phenyl, phenylmethyl, benzoyl, halobenzoyl, lower alkylcarbonyl, lower alkyloxycarbonyl and trifluoromethyl, provided that when more than 1 substituents are present only 1 thereof may be selected from the group consisting of phenyl, phenylmethyl, benzoyl and halobenzoyl.

3. A chemical compound selected from the group consisting of 1-[2-(2,4-dichlorophenyl)-4-(2-propenyloxymethyl)-1,3-dioxolan-2-ylmethyl]-1H-imidazole and the therapeutically acceptable acid addition salts thereof.

4. A chemical compound selected from the group consisting of cis-1-[2-(2,4-dichlorophenyl)-4-(2-propenyloxymethyl)-1,3-dioxolan-2-ylmethyl]-1H-imidazole and the therapeutically acceptable acid addition salts thereof.

5. A chemical compound selected from the group consisting of 1-{2-(2,4-dichlorophenyl)-4-[(2-propynyloxy)methyl]-1,3-dioxolan-2-ylmethyl}-1H-imidazole and the therapeutically acceptable acid addition salts thereof.

6. A chemical compound selected from the group consisting of cis-1-{2-(2,4-dichlorophenyl)-4-[(2-propynyloxy)methyl]-1,3-dioxolan-2-ylmethyl}-1H-imidazole and the therapeutically acceptable acid addition salts thereof.

7. A composition for combatting the growth of a microorganism selected from the group consisting of fungus and bacterium comprising an inert carrier material and as an active ingredient an effective antifungal or antibacterial amount of a compound selected from the group consisting of an amidazole derivative having the formula

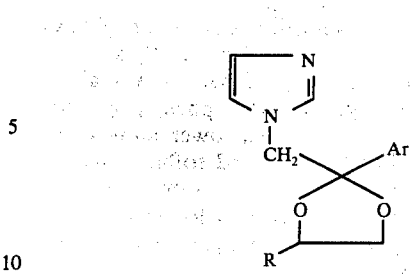

and the therapeutically active acid addition salts and stereochemical optical isomeric forms thereof, wherein:

Ar is a member selected from the group consisting of phenyl, substituted phenyl, thienyl, halothienyl and naphthalenyl, and wherein said substituted phenyl is phenyl having from 1 to 3 substituents independently selected from the group consisting of halo, lower alkyl, lower alkyloxy, nitro and cyano; and R is a member selected from the group consisting of alkyloxymethyl wherein the alkylgroup has from 1 to 10 carbon atoms, alkenyl, alkenyloxymethyl, wherein said alkenyl has from 2 to 10 carbon atoms, hydroxymethyl, 2-propynyloxymethyl, halomethyl, arylmethyl and arylmethoxymethyl, wherein said aryl is a member selected from the group consisting of phenyl, substituted phenyl, naphthalenyl and mono- and di-halonaphthalenyl, and wherein said substituted phenyl is phenyl having from 1 to 3 substituents independently selected from the group consisting of halo, lower alkyl, lower alkyloxy, cyano, nitro, phenyl, phenylmethyl, benzoyl, halobenzoyl, lower alkylcarbonyl, lower alkyloxycarbonyl and trifluoromethyl, provided that when more than 1 substituents are present only 1 thereof may be selected from the group consisting of phenyl, phenylmethyl, benzoyl and halobenzoyl.

8. A composition for combatting the growth of a microorganism selected from the group consisting of fungus and bacterium comprising an inert carrier material and as an active ingredient an effective antifungal or antibacterial amount of a compound selected from the group consisting of an imidazole derivative having the formula

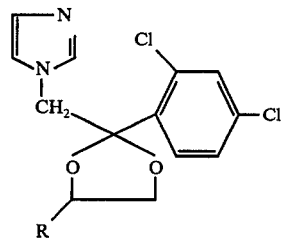

and the therapeutically active acid addition salts and stereochemical optical isomeric forms thereof, wherein:

R is a member selected from the group consisting of alkyloxymethyl wherein the alkylgroup has from 1 to 10 carbon atoms, alkenyl, alkenyloxymethyl, wherein said alkenyl has from 2 to 10 carbon atoms, hydroxymethyl, 2-propynyloxymethyl, halomethyl, arylmethyl and arylmethoxymethyl, wherein said aryl is a member selected from the group consisting of phenyl, substituted phenyl, naphthalenyl and mono- and di-halonaphthalenyl, and wherein said substituted phenyl is phenyl having from 1 to 3 substituents independently selected from the group consisting of halo, lower alkyl, lower alkyloxy, cyano, nitro, phenyl, phenylmethyl, benzoyl, halobenzoyl, lower alkylcarbonyl, lower alkyloxycarbonyl and trifluoromethyl, provided that when more than 1 substituents are present only 1 thereof may be selected from the group consisting of phenyl, phenylmethyl, benzoyl and halobenzoyl.

9. A composition for combatting the growth of a microorganism selected from the group consisting of fungus and bacterium comprising an inert carrier material and as an active ingredient an effective antifungal or antibacterial amount of a compound selected from the group consisting of 1-[2-(2,4-dichlorophenyl)-4-(2-propenyloxymethyl)-1,3-dioxolan-2-ylmethyl]-1H-imidazole and the therapeutically acceptable acid addition salts thereof.

10. A composition for combatting the growth of a microorganism selected from the group consisting of fungus and bacterium comprising an inert carrier material and as an active ingredient an effective antifungal or antibacterial amount of a compound selected from the group consisting of cis-1-[2-(2,4-dichlorophenyl)-4-(2-propenyloxymethyl)-1,3-dioxolan-2-ylmethyl]-1H-imidazole and the therapeutically acceptable acid addition salts thereof.

11. A composition for combatting the growth of a microorganism selected from the group consisting of fungus and bacterium comprising an inert carrier material and as an active ingredient an effective antifungal or antibacterial amount of a compound selected from the group consisting of 1-{2-(2,4-dichlorophenyl)-4-[(2-propynyloxy)methyl]-1,3-dioxolan-2-ylmethyl}-1H-imidazole and the therapeutically acceptable acid addition salts thereof.

12. A composition for combatting the growth of a microorganism selected from the group consisting of fungus and bacterium comprising an inert carrier material and as an active ingredient an effective antifungal or antibacterial amount of a compound selected from the group consisting of cis-1-{2-(2,4-dichlorophenyl)-4-[(2-propynyloxy)methyl]-1,3-dioxolan-2-ylmethyl}-1H-imidazole and the therapeutically acceptable acid addition salts thereof.

* * * * *